United States Patent [19]

Howard et al.

[11] Patent Number: 6,127,574
[45] Date of Patent: Oct. 3, 2000

[54] CARBONYLATION PROCESS

[75] Inventors: Mark Julian Howard, North Humberside; Michael David Jones, Yorkshire, both of United Kingdom

[73] Assignee: BP Chemicals Limited, London, United Kingdom

[21] Appl. No.: 09/097,918

[22] Filed: Jun. 16, 1998

[30] Foreign Application Priority Data

Jun. 16, 1997 [GB] United Kingdom ................... 9712596

[51] Int. Cl.$^7$ .................................................. C07C 45/50
[52] U.S. Cl. ........................... 562/519; 554/128; 560/97; 560/114; 560/207; 260/604
[58] Field of Search .................. 554/128; 560/97; 560/114, 207; 562/519; 260/604

[56] References Cited

U.S. PATENT DOCUMENTS

| | | | |
|---|---|---|---|
| 3,408,336 | 10/1968 | Benson | 260/78.4 |
| 3,560,158 | 2/1971 | Benson | 23/230 |
| 3,985,679 | 10/1976 | Taylor et al. . | |
| 4,066,705 | 1/1978 | Hughes . | |
| 4,077,906 | 3/1978 | Hughes | 252/431 |
| 4,328,125 | 5/1982 | Drago et al. . | |
| 4,394,500 | 7/1983 | Milford, Jr. | 528/313 |
| 4,460,763 | 7/1984 | Milford, Jr. | 528/336 |
| 4,800,188 | 1/1989 | Shepherd | 502/159 |
| 5,155,261 | 10/1992 | Marston et al. | 562/519 |
| 5,223,550 | 6/1993 | Hughes et al. . | |
| 5,281,359 | 1/1994 | Scates et al. | 252/182.16 |
| 5,360,929 | 11/1994 | Watson et al. | 562/891 |
| 5,364,963 | 11/1994 | Minami et al. | 562/519 |
| 5,420,313 | 5/1995 | Cunnington et al. | 549/529 |
| 5,466,874 | 11/1995 | Scates et al. | 562/519 |
| 5,807,803 | 9/1998 | Cunnington et al. | 502/155 |

FOREIGN PATENT DOCUMENTS

| | | |
|---|---|---|
| 1115688A | of 1996 | China . |
| 0 153 834 | 9/1985 | European Pat. Off. . |

OTHER PUBLICATIONS

Dazhi et al, CN Patent Appln. Specification No. 95104298.x, pp. 1–18, filed May 4, 1995, pulished Jan. 31, 1996.
Abstract: Derwent Publications Ltd., GB; AN 97–435993, XP002077608; & CN 1 115 688 A (Chem. Chinese Acad. Sci.) (1996).
Chemical Abstract: 122:3210: Lu et al., "Study on polybenzimidazole–platinum, rhodium . . . ", 430–5 (1993).
Chemical Abstract: 121:301536: Rusanov et al., "Formation, characterization and catalytic activity . . . ", 215–29 (1993);.
Derwent Abstract 97–316511/29: 95 Japanese Patent JP–303449.

*Primary Examiner*—James O. Wilson
*Assistant Examiner*—Howard Owens
*Attorney, Agent, or Firm*—Nixon & Vanderhye

[57] ABSTRACT

A process for the production of a carboxylic acid and/or a carboxylic acid anhydride which process comprises contacting a reaction composition comprising an alcohol and/or a carboxylic acid ester, optionally water, a first hydrocarbyl halide and/or a hydrocarbyl ether reactant and a second hydrocarbyl halide promoter, the first and second hydrocarbyl halides being the same or different, with carbon monoxide in the presence of a catalyst comprising an insoluble imidazole-containing resin supporting a Group VIII metal species.

22 Claims, No Drawings

CARBONYLATION PROCESS

The present invention relates in general to a process for the production of carboxylic acid and/or carboxylic acid anhydrides and in particular to such a process conducted in the presence of a carbonylation catalyst comprising a polymer supported Group VIII metal species.

Carbonylation processes are known in which small organic molecules such as alkenes, alkynes, alcohols, esters, hydrocarbyl halides or hydrocarbyl ethers are reacted with carbon monoxide in the liquid phase and in the presence of a transition metal catalyst, for example rhodium. When esters, hydrocarbyl halides or hydrocarbyl ethers are used as reactants under substantially anhydrous conditions carboxylic acid anhydrides can be produced. It is usual in such processes to use a homogeneous transition metal catalyst.

More recently, however, interest has been building in the use in carbonylation processes of heterogeneous supported rhodium catalysts as described for example in U.S. Pat. No. 4,328,125; U.S. Pat. No. 5,155,261; U.S. Pat. No. 5,364,963; and U.S. Pat. No. 5,360,929.

U.S. Pat. No. 4,328,125 describes heterogeneous anionic transition metal catalysts containing a catalytically effective amount of an anionic species having the formula $M_n(CO)_m(X)_p^{2-}$, said anionic species being ionically bonded to an insoluble cross-linked anion exchange resin containing a bound quaternary ammonium cation. Such catalysts are said to effect carbonylation and hydroformylation reactions and are said to be prepared by treating a resin containing a polymeric quaternary ammonium salt with a neutral transition metal carbonyl compound. Suitable resins are said to include polyvinyl pyridines and polystyrene bound pyridines. The examples given in the patent all relate to rhodium supported catalysts. All of the examples of carbonylation reactions take place in the presence of water and/or methanol to produce acetic acid.

U.S. Pat. No. 5,155,261 describes a process for the carbonylation of methanol to acetic acid which uses a heterogeneous catalyst comprising an insoluble polymer having pendant free base, N-oxide or quaternised pyridine groups or a combination thereof supporting a rhodium species loaded to less than about 10 weight percent (expressed as metal) of the polymer component. Most preferred catalysts are said to be porous cross-linked 4—or 2-vinylpyridine copolymers in the free base or N-oxide form which have been quaternised either preformed or in situ with an alkyl halide such as methyl iodide and loaded at about 2 weight percent by reaction with a rhodium salt such as rhodium chloride trihydrate in an initial or generation run.

U.S. Pat. No. 5,364,963 discloses a catalyst for the production of acetic acid from methanol and carbon monoxide comprising a rhodium complex supported on a porous, cross-linked vinylpyridine resin, wherein said vinylpyridine resin has a cross-linking degree of 30–60%, a pore volume of 0.2–0.4 cc/g and an average pore diameter of 20–100 nm. The catalyst is prepared by the steps comprising: (a) contacting a solid, pyridine ring—containing resin with an aqueous solution containing rhodium ion so that the rhodium is bound to said resin; and (b) contacting said rhodium ion—carrying resin with carbon monoxide and an alkyl iodide in an organic solvent so that said rhodium ion is converted to a rhodium complex bound to said resin.

Finally, U.S. Pat. No. 5,360,929 discloses a process for the production of a carboxylic acid anhydride which comprises contacting a reaction composition comprising a carboxylic acid ester, a hydrocarbyl halide and/or a hydrocarbyl ether reactant and a hydrocarbyl halide promoter with carbon monoxide in the presence of a catalyst comprising an insoluble polymer support having pendant quaternised N-base or alkylated N-oxide pyridine groups supporting a rhodium species, in which process there is maintained throughout the process a finite concentration of carboxylic acid anhydride in the reaction composition. By operating the process with a finite concentration of anhydride the reaction composition is maintained substantially anhydrous and substantially no water and/or alcohol will be present in the reaction composition.

There remains a need for improved catalysts. In the pursuit of that need we have found that the use of imidazole-containing resins as an alternative resin support to the cross-linked 4—or 2-vinylpyridine copolymers of the aforedescribed prior art can result in an enhanced rate profile without loss of selectivity in Group VIII metal catalysed carbonylation.

A class of imidazoles, namely polybenzimidazoles are known for example from U.S. Pat. No. 4,800,188, which itself refers to U.S. Pat. Nos. 3,408,336; 3,560,158; 4,394,500 and 4,460,763. U.S. Pat. No. 4,800,188 discloses a process for the production of a microporous polybenzimidazole article onto which a metalloporphyrin complex has been bound comprising:- (a) preparing a microporous polybenzimidazole shaped article; (b) reacting the microporous polybenzimidazole article with a strong base to produce a polybenzimidazole anion on the surface of the article; and (c) mixing the anionized polybenzimidazole article with a metalloporphyrin salt solution to form a microporous polybenzimidazole article supporting a metalloporphyrin complex. It is stated that the complexes can function as heterogeneous catalysts for the selective oxidation of alkanes, olefins and aromatic compounds and are useful in absorbing oxygen from a gas stream. However, there is no mention in U.S. Pat. No. 4,800,188 of the use of either a polybenzimidazole resin or a metalloporphyrin complex thereof as catalyst in a carbonylation process.

Our European Patent Application Publication No. 0623389 discloses a catalyst composition comprising molybdenum, vanadium, tungsten and/or titanium complexed to an organic or inorganic support through the intermediary of an imidazole ligand and its use in a process for the epoxidation of olefinic compounds. Polybenzimidazoles are said to be a preferred class of polymers having an imidazole ligand as part of their polymer support repeating unit. However, the use of imidazoles in carbonylation reactions is not mentioned.

Accordingly, in one aspect the present invention provides a process for the production of a carboxylic acid and/or a carboxylic acid anhydride which process comprises contacting a reaction composition comprising an alcohol and/or a carboxylic acid ester, optionally water, a first hydrocarbyl halide and/or a hydrocarbyl ether reactant and a second hydrocarbyl halide promoter, the first and the second hydrocarbyl halides being the same or different, with carbon monoxide in the presence of a catalyst comprising an insoluble imidazole-containing resin supporting a Group VIII metal species.

In the carbonylation process of the present invention the carboxylic acid ester reactant may suitably be an ester of a $C_1$ to $C_6$ carboxylic acid and a $C_1$ to $C_6$ monofunctional aliphatic alcohol. Preferably the ester reactant is an ester of a carboxylic acid and methanol, ethanol or propanol. A particularly preferred ester reactant is methyl acetate. A mixture of esters may be employed if desired. Both the first hydrocarbyl halide (reactant) and the second hydrocarbyl halide (promoter) may be any hydrocarbyl halide. Suitably the hydrocarbyl halide may be a $C_1$ to $C_6$ hydrocarbyl halide. Preferably the halide moiety of the hydrocarbyl halide is either an iodide or a bromide, more preferably an iodide. Preferred hydrocarbyl halides are alkyl iodides, of which methyl iodide, ethyl iodide or propyl iodide are more preferred. A mixture of hydrocarbyl halides may also be used. The first and the second hydrocarbyl halide (if any) may be the same or different, preferably the same. The ether reactant may be any hydrocarbyl ether. Preferably the ether is a $C_1$ to $C_6$ hydrocarbyl ether, more preferably a dialkyl ether, most preferably dimethyl ether, diethyl ether or dipropyl ether. A mixture of ethers may also be used if desired. More than one ester, halide and/or ether may be used.

In the carbonylation process of the present invention, the alcohol may suitably be an aliphatic alcohol having up to 6 carbon atoms, including methanol, ethanol, propanol, isopropanol, butanols, pentanols and hexanols. A preferred alcohol is methanol, the carbonylation product of which comprises acetic acid and/or methyl acetate. Reactive derivatives of the alcohol may also be used as an alternative. Suitably, such derivatives include dialkyl ethers and esters of alcohols having n carbon atoms with carboxylic acids having n+1 carbon atoms. Suitable reactive derivatives of methanol, for example, include methyl acetate, dimethyl ether and methyl iodide. A mixture of more than one alcohol and/or reactive derivative thereof for example a mixture of methanol and methyl acetate may also be employed.

Where the carbonylation process produces carboxylic acid, water is present in an amount greater than 0.1% up to 25% by weight based on the weight of the reaction mixture. Water is in general produced during the carbonylation process as a by-product of esterification. This water may be recycled to the reaction mixture.

Carbon monoxide used in the process of the present invention may be essentially pure or may contain inert impurities such as, for example, carbon dioxide, methane, nitrogen, noble gases and $C_1$ to $C_4$ parraffinic hydrocarbons. Hydrogen may be present as a co-promoter in the carbon monoxide.

The catalyst comprises an insoluble imidazole-containing resin supporting a Group VIII metal species. Suitable Group VIII metal species are rhodium and iridium. Examples of suitable rhodium—containing compounds for use in the preparation of the supported catalyst include $RhCl_3$ [{$Rh(CO)_2Cl$}$_2$], $RhCl_3$ hydrate, $RhBr_3$ hydrate, $RhI_3$, $Rh(OH)_3$, $RhO_3$ and $Rh(OAc)_3$.

Examples of suitable iridium-containing compounds for use in the preparation of the supported catalyst include $IrCl_3$, $IrI_3$, $IrBr_3$, [$Ir(CO)_2I$]$_2$, [$Ir(CO)_2Cl$]$_2$, [$Ir(CO)_2Br$]$_2$, [$Ir(CO)_2I_2$]$^-H^+$, [$Ir(CO)_2Br_2$]$^-H^+$, [$Ir(CO)_2I_4$]$^-H^+$, [$Ir(CH_3)I_3(CO)_2$]$^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, [$Ir_3O(OAc)_6(H_2O)_3$][OAc], and hexachloroiridic acid [$H_2IrCl_6$], preferably, chloride-free complexes of iridium such as acetates, oxalates and acetoacetates.

The Group VIII metal species on the support is present typically at 500 ppm to less than 4% metal by weight of catalyst, preferably from 0.05 to 0.4% by weight.

The catalyst may suitably further comprise a promoter. Suitably the promoter is ruthenium and/or osmium. Examples of suitable ruthenium-containing compounds which may be used in the preparation of ruthenium-promoted supported catalysts include ruthenium (III) chloride, ruthenium (III) chloride trihydrate, ruthenium (IV) chloride, ruthenium (III) bromide, ruthenium metal, ruthenium oxides, ruthenium (III) formate, [$Ru(CO)_3I_3$]$^-H^+$, tetra (aceto)chlororuthenium(II,III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis (benzene)diruthenium(II), dichloro(cycloocta-1,5-diene) ruthenium (II) polymer and tris(acetylacetonate) ruthenium (III).

Examples of suitable osmium-containing compounds which may be used in the preparation of osmium-promoted supported catalysts include osmium (III) chloride hydrate and anhydrous, osmium metal, osmium tetraoxide, triosmiumdodecacarbonyl, pentachloro-$\mu$-nitrododiosmium and mixed osmium halocarbonyls such as tricarbonyldichloroosmium (II) dimer and other organoosmium complexes.

The molar ratio of each promoter to the Group VIII metal species is suitably in the range 0.1:1 to 15:1, preferably 0.5:1 to 10:1.

The imidazole ligand component of the resin may comprise unsubstituted imidazole or a substituted imidazole such as 2-pyridyl-2-imidazole, benzimidazole, 5-benzimidazole carboxylic acid, and hydroxy-substituted imidazoles and benzimidazoles. The imidazole ligand may be attached to the support through any part of the imidazole or substituted imidazole ligand provided that the imidazole ring is available for complexing to the metal of the catalyst. The imidazole ligand may comprise part of the support rather than being pendant thereto; for example the imidazole may comprise part of a polymer repeating unit.

Suitable imidazoles for use in the present invention may have the formula

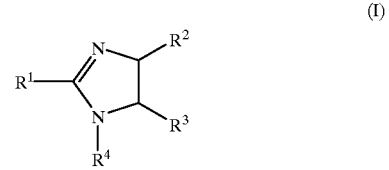

(I)

where $R^1$, $R^2$, $R^3$ and $R^4$ may be independently or together be H, alkyl, aryl, polymer or part of a ring type structure which may be hydrocarbyl or contain other heteroatoms or hetercyclic groups. The imidazole may be either within or pendant to a polymer backbone. Specific examples of such imidazoles suitable for use in the present invention are disclosed in a publication by Sherrington and Akelah in Chem. Rev. 1981, 81, 557–587.

The polymer may comprise an organic support which may be any suitable polymer and in particular one which is stable under the conditions of use of the catalyst composition. Suitable polymer supports comprise styrene polymers, methacrylate polymers, glycidyl methacrylate polymers, benzimidazole polymers, polyimides, polybenzothiazoles, polybenzoxazoles and the like, optionally copolymers with suitable comonomers and optionally cross-linked. The support may comprise a functionalised inorganic support such as functionalised silica or alumina. Preferably the support comprises a polybenzimidazole.

A preferred class of polymers for use in the catalyst of the present invention which have an imidazole ligand as part of their polymer supporting repeating unit are polybenzimidazoles.

Polybenzimidazole resins useful as supports for the rhodium species in the process of the invention include those described, for example, in U.S. Pat. No. 4,800,188. Suitable polybenzimidazoles consist essentially of recurring units of the formulae (II) and (III) as follows:

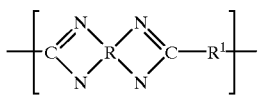
(II)

wherein R is a tetravalent aromatic nucleus, preferably symmetrically substituted, with the nitrogen atoms forming benzimidazole rings being paired upon adjacent carbon atoms, i.e. ortho carbon atoms, of the aromatic nucleus, and R′ is a member of the class consisting of (1) an aromatic ring, (2) an alkylene group (preferably one having 4 to 8 carbon atoms), and (3) a heterocyclic ring from the class consisting of (a) pyridine, (b) pyrizine, (c) furan, (d) quinoline, (e) thiophene, and (f) pyran; and

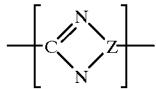
(III)

wherein Z is an aromatic nucleus having the nitrogen atoms forming the benzimidazole ring paired upon adjacent carbon atoms of the aromatic nucleus.

Preferably aromatic polybenzimidazoles are employed, e.g. polymers consisting essentially of the recurring units of the Formulae (I) and (II), wherein R′ is at least one aromatic ring or heterocyclic ring.

The polybenzimidazoles may be prepared by methods well known in the art as represented by, for example, the aforesaid U.S. Pat. No. 4,800,188; U.S. Pat. No. Re 26,065 and the book "Thermally Stable Polymers" by P. E. Cassidy and Marcel Dekker, New York (1980). Typically, the aromatic polybenzimidazoles having the recurring units of Formula (I) may be prepared by condensing an aromatic tetraamine compound containing a pair of orthodiamino subtituents on the aromatic nucleus with a dicarboxyl compound selected from the class consisting of (a) the aromatic/aliphatic esters of an aromatic dicarboxylic acid, (b) the aromatic/aliphatic esters of a heterocyclic dicarboxylic acid wherein the carboxyl groups are substituents on a carbon in a ring compound selected from the class consisting of pyridine, pyrazine, furan, quinoline, thiophene and pyran, (c) an anhydride of a dicarboxylic acid, and (d) a free aromatic or aliphatic dicarboxylic acid. The aromatic polybenzimidazoles having recurring units of Formula (II) may be prepared by self- condensing a trifunctional aromatic compound containing only a single set of ortho—disposed diamino substituents and an aromatic, preferably phenyl, carboxylate ester substituent.

Exemplary of polybenzimidazoles of the Formula (I) are:
poly-2,2′-(m-phenylene)-5,5′-bibenzimidazole;
poly-2,2′-(pyridylene-3″,5″)-5,5′-bibenzimidazole; poly-2, 2′-(furylene-2″,5″)-5,5′-bibenzimidazole
poly-2,2′-(naphthalene-1″, 6″)-5, 5′-bibenzimidazole
poly-2,2′-(biphenylene-4″, 4″)-5, 5′- bibenzimidazole
poly-2,2′-amylene-5, 5′-bibenzimidazole;
poly-2,2′-octamethylene-5, 5′-bibenzimidazole;
poly-2,6-(m-phenylene)-diimidazobenzene;
poly-2,2′-(cyclohexeneyl-5, 5′-bibenzimidazole;
poly-2,2′-(m-phenylene)-5, 5′-di(benzimidazole)ether;
poly-2,2′-(m-phenylene)-5, 5′-di(benzimidazole)sulphide;
poly-2,2′-(m-phenylene)-5, 5′-di(benzimidazole)sulfone;
poly-2,2′-(m-phenylene)-5, 5′-di(benzimidazole)methane;
poly-2,2″-(m-phenylene)-5, 5′-di(benzimidazole)propane-2, 2.

Exemplary of polybenzimidazoles of the Formula (II) is poly 2, 5 (6)-benzimidazole.

A preferred polybenzimidazole for use as a support in the present invention is poly-2, 2′-(m-phenylene)-5, 5′-bibenzimidazole, the recurring unit of which has the Formula (IV):

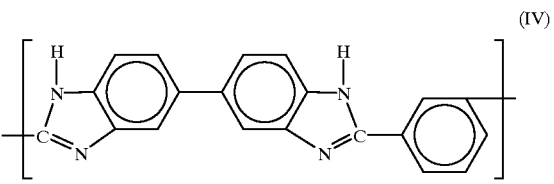
(IV)

The polybenzimidazole resin may be formed as a particulate either by emulsification—precipitation, or by atomising, non-solvent quenching procedures. Such techniques are well-known in the art.

The catalyst may suitably be prepared by reacting the polybenzimidazole resin with the rhodium species and a hydrocarbyl halide under typical carbonylation conditions either in situ or in an initial or generation run.

The process may be operated in the liquid or the vapour phase.

The process of the present invention is suitably operated at a temperature in the range from 50 to 250° C., preferably from 100 to 200° C., more preferably in the range from 150 to 200° C. The total pressure may suitably be in the range from 1 to 500 barg, preferably from 10 to 80 barg.

In a preferred embodiment the present invention provides a process for the production of acetic acid and/or acetic anhydride which process comprises contacting at elevated temperature a liquid reaction composition comprising methanol, methyl acetate, optionally water, a $C_1$ to $C_3$ alkyl iodide, preferably methyl iodide, reactant and the identical $C_1$ to $C_3$ alkyl iodide, preferably methyl iodide, promoter with carbon monoxide in the presence of a catalyst comprising an insoluble polybenzimidazole resin supporting a rhodium species.

In another aspect the present invention provides a catalyst suitable for use in a process as hereinbefore described which catalyst comprises a Group VIII metal species, other than a metalloporphyrin, supported on an imidazole-containing resin.

The invention will now be illustrated by reference to the following Comparison Test and Examples. In the Comparison Test reference is made to Reillex (TM) resin 425, which is described in U.S. Pat. No. 5,155,261 (Reilly Industries, Inc.) as being a 25% cross-linked copolymer of 4-vinylpyridine and a commercially available divinylbenzene and exhibiting a convenient insoluble bead form, high porosity, good thermal stability, and high concentration of metal binding sites. Reillex (TM) 425 is commercially available from Reilly Tar and Chemical Corporation.

In the Comparison Test and Examples the following experimental procedure was adopted:

EXPERIMENTAL PROCEDURE

All experiments were performed using a 300 ml Hastalloy B2 (Trade Mark) autoclave equipped with a Dispersimax (Trade Mark) stirrer, liquid catalyst injection facility and cooling coils. A gas supply to the autoclave was provided from a ballast vessel, feed gas being provided to maintain the autoclave at a constant pressure. The rate of gas uptake at a certain point in a reaction run was used to calculate the rate, in mol(kg.h), at a particular reactor composition (reactor composition based on a cold degassed volume).

For each batch carbonylation experiment the resin support was charged to the autoclave base assembly. The reactor was then pressure tested with nitrogen and vented via a gas sampling system. The autoclave was then flushed with hydrogen (3×5 barG). The remaining liquid components of the reaction composition were then charged to the autoclave via a liquid addition port. The autoclave was then pressurised with hydrogen (typically 1 barG) and carbon monoxide (typically 26 barG) and heated with stirring (1500 rpm) to reaction temperature. The total pressure was then raised to approximately 3 barG below the desired operating pressure by feeding forward carbon monoxide from the ballast vessel. Once stable at temperature the catalyst was injected using an over pressure of carbon monoxide. The reactor pressure was maintained constant (±0.5 barG) by feeding gas from the ballast vessel throughout the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) controller. In addition, excess heat of reaction was removed by means of cooling coils. At the end of the reaction the ballast vessel was isolated and the reactor crash cooled by use of the cooling coils. The head space gases and liquid product were sampled and analysed by gas chromatography.

COMPARISON TEST

Reillex (TM) 425 resin was sieved to give beads of greater than 300 mm in diameter. It was then washed with copious amounts of methanol and dried at 100° C. in vacuo. The water content of this resin was determined by analysis to be 1.25%. A calculated quantity of acetic anhydride was added to the reaction mixture to account for the presence of water.

The batch autoclave was charged with Reillex resin 425 (25 ml, 10.36 g). The autoclave was flushed with hydrogen. The liquid components were then added, methyl iodide (42.74 g, 0.3 moles), acetic acid (43.07 g, 0.72 moles), methyl acetate (37.68 g, 1.97 moles) and acetic anhydride (8.34 g, 0.08 moles), and then pressurised with hydrogen to an ambient pressure of 1 barG and carbon monoxide to an ambient pressure of 12 barG. The autoclave contents were stirred 1500 rpm) and heated to 185° C. Once stable at temperature the catalyst ([Rh(CO)$_2$Cl]$_2$; 0.1986 g, 0.51 mmoles) dissolved in acetic acid (12 g, 0.2 moles) was then introduced using an over pressure of carbon monoxide to give an operating pressure of 41.5 barG. The reaction was carried out at constant pressure (41.5 barG) for a period of one hour and five minutes. The methyl acetate concentration in the liquid was calculated from the carbon monoxide uptake as the reaction progressed. When the methyl acetate concentration was calculated to be 20% by weight the reaction rate was calculated to be 2.6 moles/kg/hr (417 Rh turnovers/hr). At 10% by weight methyl acetate concentration the reaction rate was 1.0 mol/kg/hr (173 Rh turnovers/hr).

This is not an example according to the present invention because the resin employed as support was not a polybenzimidazole resin as required by the present invention. It is included only for the purpose of comparison.

EXAMPLE 1

The polybenzimidazole resin was supplied as a fine powder. It was washed with copious amounts of methanol and dried at 100° C. in vacuo.

The Comparison Test was repeated except that the autoclave was charged initially with polybenzimidazole (25 ml, 16.15 g) and acetic acid (29 g, 0.48 moles). The autoclave, after flushing with hydrogen was charged with acetic acid (9.99 g, 0.166 moles), methyl iodide (49.07 g, 0.35 moles), methyl acetate (39.98 g, 0.54 moles) and acetic anhydride (10 g, 0.10 moles). The catalyst ([Rh(CO)$_2$Cl]$_2$; 0.2 g, 0.51 mmoles) dissolved in acetic acid (11.97 g, 0.2 moles) was injected when the reaction had reached elevated temperature.

When the methyl acetate concentration was calculated to be 20% by weight the reaction rate was calculated to be 3.9 moles/kg/hr (644 Rh turnovers/hr). At 10% by weight methyl acetate concentration the reaction rate was 1.78 moles/kg/hr (303 Rh turnovers/hr).

EXAMPLE 2

The polybenzimidazole resin was supplied as a fine bead. It was washed with copious amounts of methanol and dried at 100° C. in vacuo.

The Comparison Test was repeated except that the autoclave was charged initially with polybenzimidazole (25 ml, 5.81 g). The autoclave, after flushing with hydrogen was charged with acetic acid (47.9 g, 0.80 moles), methyl iodide 43.4 g, 0.31 moles), methyl acetate (40.0 g, 0.54 moles) and acetic anhydride (10.2 g, 0.10 moles). The catalyst ([Rh(CO)$_2$Cl]$_2$; 0.2 g, 0.51 mmoles) dissolved in acetic acid (12.0 g, 0.2 moles) was injected when the reaction had reached elevated temperature.

When the methyl acetate concentration was calculated to be 20% by weight the reaction rate was calculated to be 3.0 moles/kg/hr (454 Rh turnovers/hr). At 11.5% by weight methyl acetate concentration the reaction rate was 1.5 moles/kg/hr (231 Rh turnovers/hr).

We claim:

1. A carbonylation process which comprises contacting a composition comprising a reactant selected from the group consisting of an alcohol, a carboxylic acid ester, a first hydrocarbyl halide and a hydrocarbyl ether reactant, and optionally water, with carbon monoxide in the presence of a catalyst consisting essentially of a second hydrocarbyl halide promoter and an insoluble imidazole-containing resin supporting a Group VIII metal species, the first and second hydrocarbyl halides being the same or different.

2. A process as claimed in claim 1 wherein the carboxylic acid ester is an ester of a $C_1$ to $C_6$ carboxylic acid and a $C_1$ to $C_6$ monofunctional aliphatic alcohol.

3. A process as claimed in claim 1 wherein the carboxylic acid ester is methyl acetate.

4. A process as claimed in claim 1 wherein the alcohol is $C_1$ to $C_6$ alcohol.

5. A process as claimed in claim 1 wherein the alcohol is methanol.

6. A process as claimed in claim 1 wherein the hydrocarbyl halide is a $C_1$ to $C_6$ hydrocarbyl halide.

7. A process as claimed in claim 1 wherein the hydrocarbyl halide is methyl iodide, ethyl iodide or propyl iodide.

8. A process as claimed in claim 1 wherein the hydrocarbyl ether is a $C_1$ to $C_6$ hydrocarbyl ether.

9. A process as claimed in claim 1 wherein the hydrocarbyl ether is dimethyl ether, diethyl ether or dipropyl ether.

10. A process as claimed in claim 1 wherein the Group VIII metal species is present from 0.5 to 4% metal by weight of catalyst.

11. A process as claimed in claim 1 wherein the Group VIII metal species is rhodium or iridium.

12. A process as claimed in claim 11 wherein rhodium-containing compounds for use in the preparation of the supported catalyst are selected from the group consisting of $RhCl_3[\{Rh(CO)_2Cl\}_2]$, $RhCl_3$ hydrate, $RhBr_3$ hydrate, $RhI_3$, $Rh(OH)_3$, $Rh\ O_3$ and $Rh(OAc)_3$.

13. A process as claimed in claim 11 wherein iridium-containing compounds for use in the preparation of the supported catalyst are selected from the group consisting of $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$.

14. A process as claimed in claim 1 wherein the catalyst further consists of a promoter which is selected from the group consisting of ruthenium and osmium.

15. A process as claimed in claim 1 wherein the imidazole is an unsubtituted imidazole or a substituted imidazole selected from the group consisting of 2-pyridyl-2-imidazole benzimidazole, 5-benzimidazole carboxylic acid and hydroxy-substituted imidazoles and benzimidazoles.

16. A process as claimed in claim 1 wherein the imidazole is polybenzimidazole.

17. A process as claimed in claim 1, wherein the polybenzimidazole resin consists essentially of recurring units of the formula:

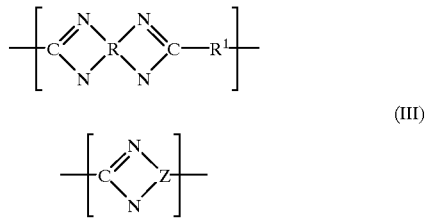

wherein R is a tetravalent aromatic nucleus with the nitrogen atoms forming benzimidazole rings being paired upon adjacent carbon atoms of the aromatic nucleus, and R' is a member selected from the group consisting of an aromatic ring; an alkylene group; and a heterocyclic ring selected from the group consisting of pyridine, pyrazine, furan, quinoline, thiophene and pyran; and Z is an aromatic nucleus having the nitrogen atoms forming the benzimidazole ring paired upon adjacent carbon atoms of the aromatic nucleus.

18. A process as claimed in claim 17 wherein R' is at least one aromatic ring or heterocyclic ring.

19. A process as claimed in claim 17 wherein the polybenzimidazole is poly-2, 2'-(m-phenylene)-5, 5'-bibenzimidazole the recurring unit being

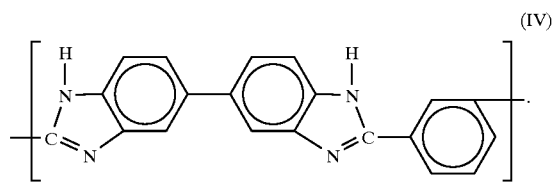

20. A process as claimed in claim 1 operated at a temperature of from 50 to 250° C. and a total pressure of from 1 to 500 barg.

21. A carbonylation process which comprises contacting at elevated temperature a reaction composition comprising a reactant selected from the group consisting of methanol, methyl acetate, and a $C_1$ to $C_3$ alkyl iodide reactant, the identical $C_1$ to $C_3$ alkyl iodide promoter, and optionally water, with carbon monoxide in the presence of a catalyst comprising an insoluble polybenzimidazole resin supporting a rhodium species.

22. A process according to claim 1 wherein the imidazole is within a polymer backbone.

* * * * *